United States Patent [19]

Boger et al.

[11] Patent Number: 4,477,441
[45] Date of Patent: Oct. 16, 1984

[54] RENIN INHIBITORS CONTAINING A C-TERMINAL DISULFIDE CYCLE

[75] Inventors: Joshua S. Boger, Bryn Mawr; Daniel F. Veber, Ambler, both of Pa.

[73] Assignee: Merck & Co., Inc., Rahway, N.J.

[21] Appl. No.: 531,969

[22] Filed: Sep. 14, 1983

[51] Int. Cl.$^3$ .................... A61K 37/00; C07C 103/52
[52] U.S. Cl. .............................. 424/177; 260/112.5 R
[58] Field of Search .................. 424/177; 260/112.5 R

[56] References Cited

PUBLICATIONS

Umezawa et al., J. Antibiot. (Tokyo) 23: 259–262, 1970.
Gross et al., Science 175:656, 1971.
Tewksbury et al., Circulation 69, 60, Supp. II: 132, Oct. 1979.
Poulsen et al., Biochim. Biophys. Acta 452:533–537, 1976.
Skeggs, Jr. et al., J. Exp. Med. 106:439–453, 1957.
Kokubu et al., Biochem. Pharmacol. 22:3217–3223, 1973.
Burton et al., Biochemistry 14:3892–3898, 1975.
Poulsen et al., Biochemistry 12:3877–3882, 1973.
Haber and Burton, Fed. Proc. Fed. Am. Soc. Exp. Biol. 38:2768–2773, 1979.
Hypertension, 4, Supp. 2, 59 (1981).
Powers et al., Acid Proteases, Structure, Function and Biology, Plenum Press, 1977, 141–157.
Tang et al., Trends in Biochem. Sci., 1:205–208, 1976.
J. Biol. Chem. 251:7088–7094, 1976.
Nakaie et al., Biochem. J. 205:43–47, 1982.
Marshall, Federation Proc. 35:2494–2501, 1976.
Burton et al., Proc,. Natl. Acad. Sci. USA 77:5476–5479, Sep. 1980.
Suketa et al., Biochemistry 14:3188, 1975.
Swales, Pharmac. Ther. 7:173–201, 1979.
Kokubu et al., Nature 217:456–457, Feb. 3, 1968.
Matsushita et al., J. Antibiotics 28:1016–1018.
Lazar et al., Biochem. Pharma. 23:2776–2778, 1974.
Miller et al., Biochem. Pharma. 21:2941–2944, 1972.
Haber, Clinical Science 59:7s–19s, 1980.
Rich et al., J. Org. Chem. 43:3624, 1978.
J. Med. Chem. 23:27, 1980.

*Primary Examiner*—Delbert R. Phillips
*Attorney, Agent, or Firm*—Raymond M. Speer; Hesna J. Pfeiffer

[57] ABSTRACT

Renin inhibitory peptides of the formula $$A-B-B-D-E-N(H)-C(H)(R^3)-C(O)-N(...)-...-F \quad (I.)$$

and analogs thereof inhibit renin and are useful for treating various forms of renin-associated hypertension and hyperaldosteronism.

8 Claims, No Drawings

RENIN INHIBITORS CONTAINING A C-TERMINAL DISULFIDE CYCLE

BACKGROUND OF THE INVENTION

1. Field of the Invention

The present invention is concerned with novel peptides which inhibit renin.

The present invention is also concerned with pharmaceutical compositions containing the novel peptides of the present invention as active ingredients, with methods of treating renin-associated hypertension and hyperaldosteronism, with diagnostic methods which utilize the novel peptides of the present invention, and with methods of preparing the novel peptides of the present invention.

Renin is a proteolytic enzyme of molecular weight about 40,000, produced and secreted by the kidney. It is secreted by the juxtaglomerular cells and acts on the plasma substrate, angiotensinogen, to split off the decapeptide angiotensin I, which is converted to the potent pressor agent angiotensin II. Thus, the renin-angiotensin system plays an important role in normal cardiovascular homeostasis and in some forms of hypertension.

In the past, attempts to modulate or manipulate the renin-angiotensin system have met with success in the use of inhibitors of angiotensin I converting enzyme. In view of this success, it seems reasonable to conclude that a specific inhibitor of the limiting enzymatic step that ultimately regulates angiotensin II production, the action of renin on its substrate, would be at least equally successful. Thus, an effective inhibitor of renin has been long sought as both a therapeutic agent and as an investigative tool.

2. Brief Description of the Prior Art

There has been substantial interest in the synthesis of useful renin inhibitors for many decades; and the following table lists the major classes of renin inhibitors that have been studied, as well as their inhibition constants ($K_i$):

| Class | $K_i$ (M) |
|---|---|
| Renin antibody | probably |
| Pepstatin | $10^{-6}$–$10^{-7}$ |
| Phospholipids | $10^{-3}$ |
| Substrate analogs | $10^{-3}$ Octa-to |
| Tetrapeptides | |
| tridecapeptides | $10^{-5}$–$10^{-6}$ |

Umezawa et al., in *J. Antibiot.* (Tokyo) 23: 259–262, 1970, reported the isolation of a peptide from actinomyces that was an inhibitor of aspartyl proteases such as pepsin, cathepsin D, and renin. This peptide, known as pepstatin, was found by Gross et al., *Science* 175: 656, 1971, to reduce blood pressure in vivo after the injection of hog renin into nephrectomized rats. However, pepstatin has not found wide application as an experimental agent because of its limited solubility and its inhibition of a variety of other acid proteases in addition to renin. The structure of pepstatin is shown below:

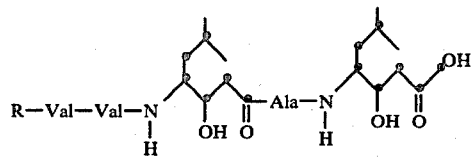

To date, many efforts have been made to prepare a specific renin inhibitor based on substrate analogy. Since the human renin substrate has only recently been elucidated (Tewksbury et al., *Circulation* 59, 60, Supp. II: 132, Oct. 1979), heretofore substrate analogy has been based on the known pig renin substrate. While the human and pig renin substrates are not the same, the substrate analogy based on pig renin has always been considered acceptable in the art as predictive of human renin inhibitory activity because of the closely related activity of the two renins. Thus, while pig renin does not cleave the human renin substrate, human renin, on the other hand, does cleave the pig renin substrate. See Poulsen et al., *Biochim. Biophys. Acta* 452: 533–537, 1976; and Skeggs, Jr. et al., *J. Exp. Med.* 106: 439–453, 1957. Moreover, the human renin inhibitory activity of the peptides of the present invention most active in inhibiting pig renin has been confirmed, thus providing further evidence of this accepted correlation between human and pig renin activity.

It has been found, for example, using pig renin substrate analogy, that the octapeptide sequence extending from histidine-6 through tyrosine-13 has kinetic parameters essentially the same as those of the full tetradecapeptide renin substrate. The amino acid sequence of the octapeptide in pig renin substrate is as follows:

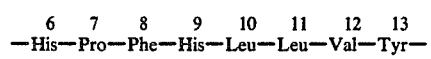

Renin cleaves this substrate between Leu[10] and Leu[11].

Kokubu et al., *Biochem. Pharmacol.* 22: 3217–3223, 1973, synthesized a number of analogs of the tetrapeptide found between residues 10 to 13, but while inhibition could be shown, inhibitory constants were only of the order of $10^{-3}$M.

Analogs of a large segment of renin substrate were also synthesized: Burton et al., *Biochemistry* 14: 3892–3898, 1975, and Poulsen et al., *Biochemistry* 12: 3877–3882, 1973. Two of the major obstacles which had to be overcome to obtain an effective renin inhibitor useful in vivo were lack of solubility and weak binding (large inhibitory constant). Modifications to increase solubility soon established that the inhibitory properties of the peptides are markedly dependent on the hydrophobicity of various amino acid residues, and that increasing solubility by replacing lipophilic amino acids with hydrophilic isosteric residues becomes counterproductive. Other approaches to increasing solubility have had limited success. Various modifications designed to increase binding to renin have also been made, but here too, with only limited success. For a more detailed description of past efforts to prepare an effective inhibitor of renin, see Haber and Burton, *Fed. Proc. Fed. Am. Soc. Exp. Biol.* 38: 2768–2773, 1979.

More recently, Hallett, Szelke, and Jones, in work described in European Patent Publication No. 45,665 *Nature*, 299, 555 (1982), and *Hypertension*, 4, Supp. 2, 59 (1981), have replaced the Leu-Leu site of renin cleavage by isosteric substitution, and obtained compounds with excellent potency.

Powers et al., in *Acid Proteases, Structure, Function and Biology*, Plenum Press, 1977, 141–157 have suggested that in peptstatin, statine occupies the space of the two amino acids on either side of the cleavage site of a pepsin substrate, and Tang et al., in *Trends in Biochem. Sci.*, 1: 205–208 (1976) and *J. Biol. Chem.*, 251: 7088–94, 1976, have proposed that the statine residue of pepstatin resembles the transition state for pepsin hydrolysis of peptide bonds. However, the applicability of these concepts to renin inhibitors is not taught in any of these references, and would be speculative due to the known high degree of specificity of the renin enzyme.

Nakaie et al., *Biochem. J.* 205: 43–47, 1982, describe inhibition of renin by conformationally restricted analogs of angiotensinogen involving a disulfide bond between residues 5 and 10. However, the cyclical inhibitors of the present invention are neither described nor suggested.

For other articles describing previous efforts to devise renin inhibitors, see Marshall, *Federation Proc.* 35: 2494–2501, 1976; Burton et al., *Proc. Natl. Acad. Sci. U.S.A.* 77: 5476–5479, Sept. 1980; Suketa et al., *Biohemistry* 14: 3188, 1975; Swales, *Pharmac. Ther.* 7: 173–201, 1979; Kokubu et al., *Nature* 217: 456–457, Feb. 3, 1968; Matsushita et al., *J. Antibiotics* 28: 1016–1018, Dec. 1975; Lazar et al., *Biochem. Pharma.* 23: 2776–2778, 1974; Miller et al., *Biochem. Pharma.* 21: 2941–2944, 1972; Haber, *Clinical Science* 59: 7s–19s, 1980; and Rich et al., *J. Org. Chem.* 43: 3624, 1978, and *J. Med. Chem.* 23: 27, 1980.

DETAILED DESCRIPTION OF THE INVENTION AND PREFERRED EMBODIMENTS

In accordance with the present invention there are provided renin inhibitory peptides of the formula:

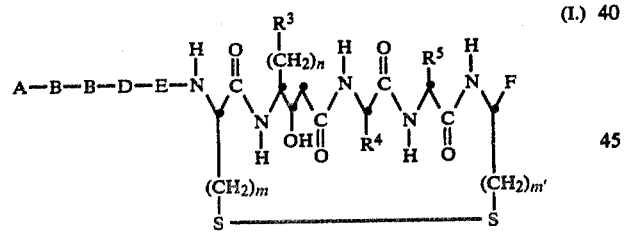
(I.)

wherein:
A is hydrogen; or

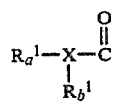

where X is —O—;

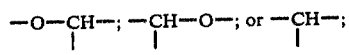

and $R_a^1$ and $R_b^1$ may be the same or different and are hydrogen; Y—$(CH_2)_p$— or Y—$(CH_2)_{p'}$—CH=CH—$(CH_2)_{p''}$, where Y is hydrogen; $C_{1-4}$alkyl; aryl; $C_{3-7}$cycloalkyl; or $C_{3-7}$cycloalkyl or aryl substituted with up to five members independently selected from the group consisting of $C_{1-8}$alkyl, trifluoromethyl, hydroxy, $C_{1-4}$alkoxy, and halo; p is 0 to 5; and p' and p'' are independently 0 to 2; except that where X is —O—, only one of $R_a^1$ or $R_b^1$ is present;

B is absent; glycyl; sarcosyl; or

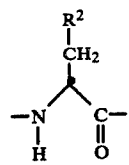

wherein $R^2$ is hydrogen; $C_{1-4}$ alkyl; hydroxy $C_{1-4}$ alkyl; aryl; aryl substituted with up to three members selected from the group consisting of $C_{1-4}$alkyl, trifluoromethyl, hydroxy, $C_{1-4}$alkoxy, and halo; indolyl; 4-imidazolyl; amino $C_{2-4}$ alkyl; guanidyl $C_{2-3}$ alkyl; or methylthiomethyl;

D is absent; or

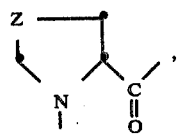

where Z is —$(CH_2)_q$— and q is 1 or 2; or —S—;
E is absent; or

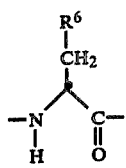

where $R^6$ is hydrogen; $C_{1-4}$alkyl; aryl; aryl $C_{1-4}$alkyl; or aryl $C_{1-4}$alkyl or aryl where the aryl portion is substituted with up to three members selected from the group consisting of $C_{1-4}$alkyl, trifluoromethyl, hydroxy, $C_{1-4}$alkoxy, and halo; or indolyl;

F is hydrogen;

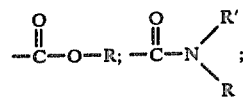

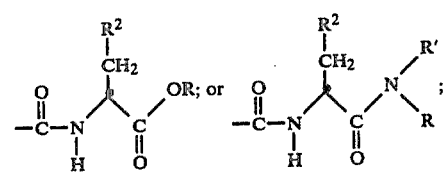

where R and R' are independently hydrogen or $C_{1-4}$alkyl;
$R^3$ is $C_{3-6}$alkyl; $C_{3-7}$ cycloalkyl; aryl; or $C_{3-7}$cycloalkyl or aryl substituted with up to three members selected from the group consisting of $C_{1-4}$alkyl, trifluoromethyl, hydroxy, $C_{1-4}$alkoxy, and halo;
$R^4$ is hydrogen; or

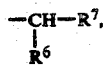

where $R^7$ is hydrogen; $C_{1-4}$alkyl; hydroxy; or $C_{3-7}$cycloalkyl; and $R^6$ is as defined above;
$R^5$ is hydrogen;

where $R^6$ and $R^7$ are as defined above; or $-(CH_2)_r-R^8$, where r is 0 or 1-4; and $R^8$ is heterocyclic; heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino; guanidyl $C_{2-3}$alkyl; or amino $C_{1-4}$alkyl;
m and m' are independently 1 or 2;
n is 1 to 4; and
wherein all of the asymmetric carbon atoms have an S configuration, except for those in the A, B, D, and F substituents, and at the junction of F, which may have an S or R configuration; and a pharmaceutically acceptable salt thereof.

while both the S and R chiralities for asymmetric carbon atoms in the A, B, D, and F substituents, and at the junction of F, are included in the peptides of the present invention, preferred chiralities are indicated in the description which follows.

In the above definitions, the term "alkyl" is intended to include both branched and straight chain hydrocarbon groups having the indicated number of carbon atoms.

The term "halo" means fluoro, chloro, bromo and iodo.

The aryl substituent represents phenyl, and naphthyl.

The heterocyclic substituent recited above represents any 5- or 6-membered aromatic ring containing from one to three heteroatoms selected from the group consisting of nitrogen, oxygen, and sulfur; having various degrees of saturation; and including any bicyclic group in which any of the above heterocyclic rings is fused to a benzene ring. Heterocyclic substituents in which nitrogen is the heteroatom are preferred, and of these, those containing a single nitrogen atom are preferred. Fully saturated heterocyclic substituents are also preferred. Thus, piperidine is a preferred heterocyclic substituent. Other preferred heterocyclic substituents are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Where the heterocyclic substituent itself is substituted, it is preferred that the substituent be aryl $C_{1-4}$alkyl.

The novel renin inhibitory peptides of the present invention may also be described in terms of common amino acid components and closely related analogs thereof, in accordance with the following formula:

$$A-B-B-D-E-G-Sta-H-I-(F) \qquad (II)$$

The A, B, D, and E components correspond to the same portions of Formula I, and the (F) component includes the F substituent of Formula I.

In Formula II, Sta represents the unusual amino acid statine and its closely related analogs, and its presence constitutes a unique feature of the renin inhibitory peptides of the present invention. Statine may be named as 4(S)-amino-3(S)-hydroxy-6-methylheptanoic acid, and may be represented by the following formula:

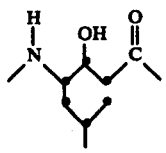

As shown in Formula III above, the delta-substituent in naturally-occurring statine is isopropyl, or a leucine sidechain, essentially. As shown in Formula I by the $R^3$ substituents, the isopropyl group may be replaced by higher alkyl groups up to six carbon atoms, cycloalkyl groups containing from three to seven carbon atoms, aryl, and $C_{3-7}$cycloalkyl or aryl substituted with up to three members selected from the group consisting of $C_{1-4}$alkyl, trifluoromethyl, hydroxy, $C_{1-4}$alkoxy, fluoro, chloro, bromo, and iodo. A phenyl substituent and a cyclohexyl substituent are especially preferred. These modifications of the naturally-occurring statine structure are in accordance with the hydrophobicity considered necessary to maintain the inhibitory activity of the total peptide.

The remaining common amino acid components of Formula II are as follows:
A has the same meaning as above in Formula I;
B is Gly, Sar, Ala, Leu, Ser, Thr, Phe, Tyr, Trp, His, Lys, Orn, Arg, or Met;
D is Pro;
E is Ala, Leu, Phe, Tyr, or Trp;
G is one end of the cyclical structure: Cys or Hcys;
H is Gly, Ala, Val, Leu, Ile, Ser, Thr, Phe, Tyr, or Trp;
I is the same as H and may also be Lys, Orn, Arg, or His; and
(F) is the other end of the cyclical structure: Cys or Hcys, and may additionally include an amino acid as in B.

It will be understood that closely related analogs of the above common amino acids, for example, aliphatic amino acids in addition to Ala, Val, Leu, and Ile, such as α-aminobutyric acid (Abu), and substituted phenyl derivatives of Phe, are included in the broad description of the novel inhibitory peptides of the present invention represented by Formula I and its definitions. Thus, the peptides of Formula II and its definitions, including the derivatives of naturally-occurring statine represented by the definitions of the $R^3$ substituent in Formula I, represent preferred peptides of the present invention.

Preferred inhibitory peptides of the present invention are the following:

```
IBU¹—His—Pro—Phe—Cys—Sta—Leu—Phe—NH
                     └─S────────S─────┘
```

-continued

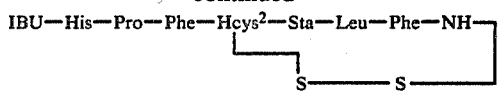

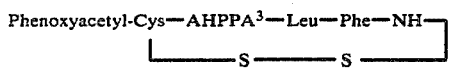

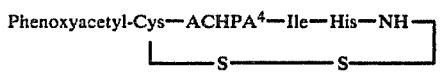

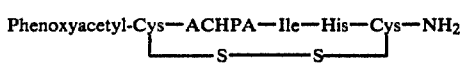

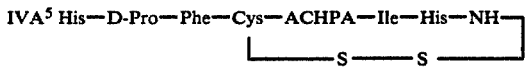

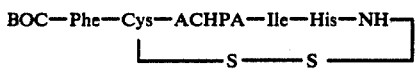

[1]IBU = Iso-butyryl.
[2]Hcys = L-homocysteine
[3]AHPPA = (3S, 4S)—4-Amino-3-hydroxy-5-phenyl-pentanoic acid.
[4]ACHPA = (3S, 4S)—4-Amino-5-cyclohexyl-3-hydroxy-pentanoic acid.
[5]IVA = Iso-valeryl.
[6]BOC = Tert-butyloxycarbonyl.

The inhibitory peptides of the present invention may be better appreciated in terms of substrate analogy from the following illustration of Formula I alongside the octapeptide sequence of a portion of the pig renin substrate, which renin cleaves between Leu[10] and Leu[11]:

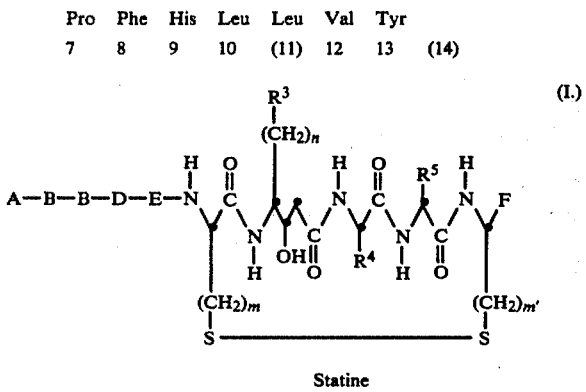

As can be seen, a unique aspect and essential feature of the present invention is the substitution of the single statine amino acid component for the double amino acid sequence: Leu[10]-Leu[11] in the endogenous pig renin substrate. It is believed that substitution of statine for both leucine amino acids rather than just one leucine results in an improved substrate analogy due to the greater linear extent of statine as compared to a single leucine component. Thus, statine more closely approximates Leu-Leu in linear extent, and thereby provides a better "fit" to the renin enzyme.

The inhibitory peptides of the present invention may also be better appreciated in terms of substrate analogy from the following illustration of Formula I alongside the octapeptide sequence of a portion of the human renin substrate, which renin cleaves between Leu[10] and Val[11]:

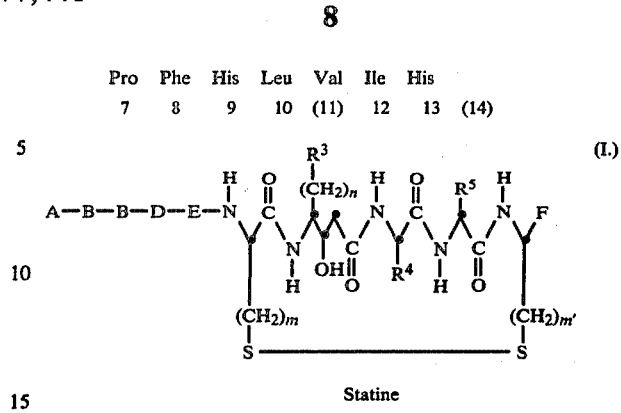

As can be seen, a unique aspect and essential feature of the present invention is the substitution of the single statine amino acid component for the double amino acid sequence: Leu[10]-Val[11] in the endogenous human renin substrate. It is believed that substitution of statine for both the leucine and valine amino acids rather than just the leucine results in an improved substrate analogy due to the greater linear extent of statine as compared to a single leucine component. Thus, statine more closely approximates Leu-Val in linear extent, and thereby provides a better "fit" to the human renin enzyme.

In the endogenous substrate it is also preferred to substitute Leu for Val[12] and Phe for Tyr[13] in order to enhance the inhibitory activity of the resulting peptide.

The Formula I compounds can be used in the form of salts derived from inorganic or organic acids and bases. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The novel peptides of the present invention possess an excellent degree of activity in treating renin-associated hypertension and hyperaldosteronism.

For these purposes the compounds of the present invention may be administered parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The peptides of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order of 2 to 35 grams per day are useful in the treatment of the above indicated conditions. For example, renin-associated hypertension and hyperaldosteronism are effectively treated by the administration of from 30 milligrams to 0.5 grams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Thus, in accordance with the present invention there is further provided a pharmaceutical composition for treating renin-associated hypertension and hyperaldosteronism, comprising a pharmaceutical carrier and a therapeutically effective amount of a peptide of the formula:

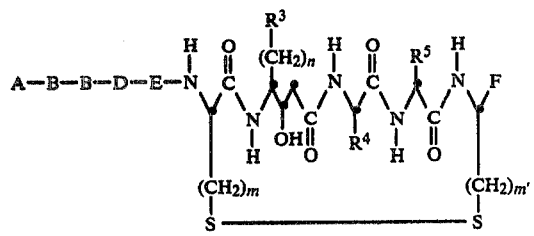

wherein A, B, D, E, R³, R⁴, R⁵ and F have the same meaning as recited further above for Formula I; wherein all of the asymmetric carbon atoms have an S configuration, except for those in the A, B, D, and F substituents, and at the junction of F, which may have an S or R configuration; and a pharmaceutically acceptable salt thereof.

Also, in accordance with the present invention there is still further provided a method of treating renin-associated hypertension and hyperaldosteronism, comprising administering to a patient in need of such treatment, a therapeutically effective amount of a peptide of the formula:

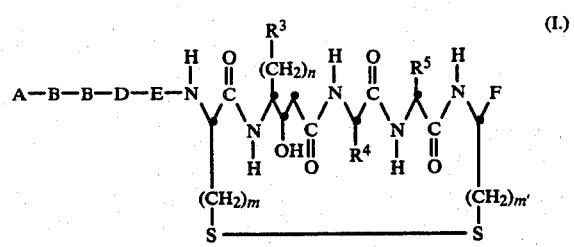

wherein A, B, D, E, R³, R⁴, R⁵ and F have the same meaning as recited further above for Formula I; wherein all of the asymmetric carbon atoms have an S configuration, except for those in the A, B, D, and F substituents, and at the junction of F, which may have an S or R configuration; and a pharmaceutically acceptable salt thereof.

The renin inhibitory novel peptides of the present invention may also be utilized in diagnostic methods for the purpose of establishing the significance of renin as a causative or contributory factor in hypertension or hyperaldosteronism in a particular patient. For this purpose the novel peptides of the present invention may be administered in a single dose of from 0.1 to 10 mg per kg of body weight.

Both in vivo and in vitro methods may be employed. In the in vivo method, a novel peptide of the present invention is administered to a patient, preferably by intravenous injection, although parenteral administration is also suitable, at a hypotensive dosage level and as a single dose, and there may result a transitory fall in blood pressure. This fall in blood pressure, if it occurs, indicates supranormal plasma renin levels.

An in vitro method which may be employed involves incubating a body fluid, preferably plasma, with a novel peptide of the present invention and, after deproteinization, measuring the amount of angiotensin II produced in nephrectomized, pentolinium-treated rats. Another in vitro method involves mixing the plasma or other body fluid with a novel peptide of the present invention and injecting the mixture into a test animal. The difference in pressor response with and without added peptide is a measure of the renin content of the plasma.

Pepstatin may be employed in the methods described above as an active control. See, e.g., U.S. Pat. Nos. 3,784,686 and 3,873,681 for a description of the use of pepstatin in diagnostic methods of this type.

The novel peptides of the present invention may be prepared in accordance with well-known procedures for preparing peptides from their constituent amino acids, which will be described in more detail below. The unusual amino acid, statine, may be prepared in accordance with the procedure described by Rich et al., *J. Org. Chem.* 43: 3624 (1978).

A general method of preparation may be described in the following terms; wherein amino acids forming peptides of various lengths are sequentially assigned a Roman numeral for each peptide, rather than on the basis of a position in the overall peptide Formula I:

A method of preparing a peptide of formula I, said peptide being comprised of from four to ten amino acids identified as I through X, amino acid (AA) I being at the C-terminus of said peptide, which substituent F comprises (F may also be AA I and II, or when F=H, then the C-terminus is an amine, or descarboxy amino acid), and amino acid (AA) IV through X, depending upon the number of amino acids present, being at the N-terminus of said peptide, to which substituent A is attached, said peptide of Formula I being cyclical by virtue of a disulfide bond between F (where F=H), AA I, or II, and AA IV, V, or VI, respectively, comprising the steps of:

(A) treating an ester of the C-terminus amino acid (AA I) with the next adjacent amino acid (AA II) of said peptide, the amino group of said amino acid being protected by a protecting group, in the presence of a condensing agent, whereby a dipeptide of the two amino acids (AA I and II) is formed;

(B) deprotecting the dipeptide formed in Step (A) by removing the protecting group from the amino group of AA II;

(C) repeating the procedures of Steps A and B successively to form a pentapeptide to a decapeptide of AA's I-II-III-IV-V, or additionally each of AA's VI through X, without, however, removing the protecting group from the amino group of AA VI through X; and providing a protecting group on the sulfur atoms of AA's I or II, and V, or VI, respectively;

(D) forming a loweralkyl ester of AA I, if said ester is not employed initially;

(E) where F=H and the disulfide bond is between F and AA IV, the procedures of Steps A through D are carried out to achieve the peptide of desired linear extent, after which it is treated with thiomethylamine or thioethylamine in which the sulfur atom is protected, to provide a protected peptide of Formula I in which F=H; after which cyclization may be carried out as described below;

(F) cyclizing the pentapeptide to decapeptide or peptide of Step E by forming a disulfide bond between F (where F=H), AA I, or II, and AA IV, V, or VI, respectively, through deprotection of the sulfur atoms followed by oxidative coupling to give the peptide of Formula I wherein A is hydrogen;

(G) removing the protecting group from the amino group of AA IV through X;

(H) treating the cyclical tetrapeptide to decapeptide formed in Step (E) with

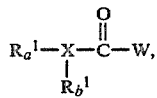

where X, $R_a^1$, and $R_b^1$ are as defined above and W is an acid halide, anhydride, or other carbonyl activating group, to give the peptide of Formula I wherein A is other than hydrogen; said method also comprising where necessary, protection of sidechain substituents of the component amino acids AA I through AA X, with deprotection being carried out as a final step; said method also comprising any combination of the steps set out above, whereby the amino acids I through X and substituents A and F are assembled in any desired order to prepare the peptide of Formula I; said method also comprising employment of the steps set out above in a solid phase sequential synthesis, whereby in the initial step the carboxyl group of the selected amino acid is bound to a synthetic resin substrate while the amino group of said amino acid is protected, followed by removal of the protecting group, the succeeding steps being as set out above, the peptide as it is assembled being attached to said synthetic resin substrate; followed by a step of removing the peptide from said synthetic resin substrate by transesterification with methanol to give the methyl ester of AA I, followed by hydrolysis and cyclization as recited above; removal of sidechain protecting groups being accomplished either before or after removal of the peptide from said synthetic resin substrate; the steps of cyclization and formation of the A and F substituents in said method being accomplished at any time and in any order during preparation of peptides of different linear extent.

A preferred method involves preparation of the peptide of desired linear extent and desired A substituent by solid phase sequential synthesis, which is then removed by transesterification to give the linear, protected (N-terminus) methyl ester in which the sulfur atoms to form the disulfide bond are also blocked, for example with the acetamidomethyl (AcM) group.

Where, for example, the C-terminal thiol-containing residue is not an amino acid, as in the partial structure:

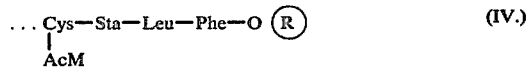

where (R) represents the resin substrate used in the solid phase sequential synthesis, the residue corresponding to:

is added to the C-terminus in its S-AcM protected form, with suitable protection of the F substituent, if required. For example, if the F substituent is carboxy, protection would be afforded by OMe esterification. The C-terminal acid of (IV) is liberated by hydrolysis, and coupling with (V) is effected using any of a variety of standard peptide coupling reagents, for example, diphenylphosphorylazide. This coupling gives:

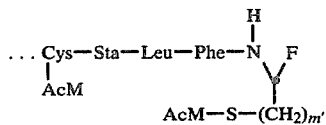

Cyclization is effected using excess iodine in dimethylformamide or dimethylformamide in water, quenching after 15–30 minutes with excess zinc dust, and filtering to give the desired cyclized peptide. The N-terminus protecting group, preferably tert-butyloxycarbonyl (BOC), is removed with trifluoroacetic acid, liquid hydrofluoric acid, or hydrochloric acid in ethyl acetate, containing 1% ethanediol, to give the free amino compound, as its salt.

The phenyl analog of statine, (3S,4S)-4-amino-3-hydroxy-5-phenylpentanoic acid (AHPPA) can be prepared in accordance with the procedure described by Rich et al., *J. Med. Chem.* 23: 27–33 (1980).

Other analogs of statine may be prepared in a straightforward manner. For example, the cyclohexylalanine analog of statine, (3S, 4S)-4-amino-5-cyclohexyl-3-hydroxypentanoic acid (ACHPA) can be prepared by catalytic hydrogenation (using $H_2$/Rh on alumina, or other suitable catalyst) of the BOC-AHPPA, prepared as described in the paragraph immediately above. Alternatively, this and similar statine analogs can be prepared in accordance with the procedure described for statine, where the BOC-Leu starting material is replaced with the amino acid containing the desired side chain. Thus, BOC-ACHPA can also be prepared starting from BOC-L-cyclohexylalanine, itself prepared, for example, by catalytic reduction of BOC-Phe, in the same manner as described for BOC-AHPPA.

The novel inhibitory peptides of the present invention are prepared by using the solid phase sequential synthesis technique.

In the following description several abbreviated designations are used for the amino acid components, certain preferred protecting groups, reagents and solvents. The meanings of such abbreviated designations are given below in Table I.

TABLE I

| Abbreviated Designation | Amino Acid |
|---|---|
| AHPPA | (3S,4S)—4-amino-3-hydroxy-5-phenylpentanoic acid |
| ACHPA | (3S,4S)—4-amino-5-cyclohexyl-3-hydroxypentanoic acid |
| Ala | L-alanine |
| Arg | L-arginine |
| Cys | L-cysteine |
| DAB | 2-S—amino-4-aminobutyric acid |
| Gly | L-glycine |
| Hcys | homocysteine, 2-amino-4-mercaptobutyric acid |
| His | D or L-histidine |
| Ile | L-isoleucine |
| Leu | L-leucine |
| Lys | L-lysine |
| Met | L-methionine |
| Orn | L-ornithine |
| Phe | L-phenylalanine |
| Ser | L-serine |
| Sar | L-sarcosine (N—methylglycine) |
| Sta | (3S,4S)—statine |
| Thr | L-threonine |
| Trp | L-tryptophan |
| Tyr | L-tyrosine |
| Val | L-valine |

| Abbreviated Designation | Protecting Groups |
|---|---|
| ACM | acetamidomethyl |
| BOC | tert-butyloxycarbonyl |
| CBZ | benzyloxycarbonyl |
| 2-Cl—CBZ | 2-chlorobenzyloxycarbonyl |
| IBU | iso-butyryl |
| IVA | iso-valeryl |
| DNP | dinitrophenyl |
| OMe | methyl ester |

| Abbreviated Designation | Activating Groups |
|---|---|
| HBT | 1-hydroxybenzotriazole |

| Abbreviated Designation | Condensing Agents |
|---|---|
| DCCI | dicyclohexylcarbodiimide |
| DPPA | diphenylphosphorylazide |

| Abbreviated Designation | Reagents |
|---|---|
| TEA | triethylamine |
| TFA | trifluoroacetic acid |

| Abbreviated Designation | Solvents |
|---|---|
| A | ammonium hydroxide (conc.) |
| AcOH | acetic acid |
| C | chloroform |
| DMF | dimethylformamide |
| E | ethyl acetate |
| M | methanol |
| P | pyridine |
| THF | tetrahydrofuran |
| W | water |

The synthesis of the peptides of the present invention by the solid phase technique is conducted in a stepwise manner on chloromethylated resin. The resin is composed of fine beads (20–70 microns in diameter) of a synthetic resin prepared by copolymerization of styrene with 1–2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as ONP ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoroacetic acid, or hydrogen chloride in ethyl acetate).

The OH group of Thr and Ser can be protected by the Bzl group and the -amino group of Lys can be protected by the INOC group or the 2-chlorobenzyloxycarbonyl (2-Cl-CBZ) group. Neither group is affected by TFA, used for removing BOC protecting groups. After the peptide is formed, the protective groups, such as 2-Cl-CBZ and Bzl, can be removed by treatment with HF or by catalytic hydrogenation.

The thiol group of Cys and Hcys can be protected with the acetamidomethyl (ACM) group, preferred as described in the examples, or by other well-known protecting groups, such as benzyl. The ACM group is best removed during cyclization with iodine, although it can be removed before cyclization with mercury, followed by iodine or air oxidation for cyclization.

After the peptide has been formed on the solid phase resin, it may be removed from the resin by a variety of methods which are well known in the art. For example the peptide may be cleaved from the resin with hydrazine, by ammonia in methanol, or by methanol plus a suitable base.

Preparation of the novel inhibitory peptides of the present invention utilizing the solid phase technique is illustrated in the following examples, which however, are not intended to be any limitation of the present invention.

EXAMPLE 1

$N^\alpha$-Butyloxycarbonyl-S-(Acetamidomethyl)-L-Homocysteine

This blocked amino acid derivative used in the subsequent syntheses was prepared according to modifications of literature procedures.

L-S-benzylhomocysteine was prepared according to the method of C. A. Dekker and J. S. Fruton, *J. Biol. Chem.* 173 471 (1948), starting from L-methionine in 27% overall yield. The S-benzyl group was removed following the procedures of V. du Vigneaud and W. I. Patterson, *J. Biol. Chem.* 109 97 (1935), and of H. Dyer, *J. Biol. Chem.* 124 519 (1938), giving free L-homocysteine. Protection of the free thiol group as the S-acetamido methyl was accomplished following the procedures described by P. Marbach and J. Rudinger, *Helv. Chim. Acta.* 57 403 (1974) for similar protection of cysteine. This procedure, using acetamidomethanol and hydrofluoric acid at low temperature gave a crude product containing predominantly the desired S-acetamidomethyl-L-homocysteine. This mixture was reacted with di-tert-butylbicarbonate (BOC$_2$O) in DMF containing diisopropylethylamine to give after workup the title crude protected amino acid. The product ($R_f$=0.44, TLC 80:20:2; chloroform:methanol:acetic acid:water) is contaminated with some side product at $R_f$=0.63. This side product can be easily removed by silica gel chromatography giving the pure BOC-(Acm)-L-homocysteine.

EXAMPLE 2 man 990B peptide synthesizer to carry out the operations according to the attached programs. The starting polymer is BOCPhe esterified to 2% cross-linked polystyrenedivinylbenzene (2 mmole, 1.7 g). The N-BOC derivatives of L-Homocys(Acm), Pro, Phe, and Leu are coupled using DCCI with an equivalent of the additive 1-hydroxybenzotriazole. The L-Homocysteine derivative is prepared as described in Example 1. The Sta derivative (BOC) is prepared in accordance with Rich, et al., *J. Org. Chem.* 43 3624 (1978). The BOC group is removed with 40% TFA. In all BOC-removal steps following the introduction of Homocys (or Cys in other examples), 1% ethanedithiol is added to the 40% TFA solution in dichloromethane (CH$_2$Cl$_2$) as a scavenger to protect the sulfur atom from side reactions during the BOC-removal. A coupling of 30 minutes followed by a recoupling of 60 minutes (2.5 equivalents each time of BOC-amino acid in 1:1 CH$_2$Cl$_2$/DMF with DCCI and HBT.H$_2$O) are used for each amino acid except Sta and Hcys. In order to conserve supplies of these two rarer amino acids, an initial coupling of 1.25 equivalents of BOC-amino acid with DCCI and HBT.H$_2$O in 1.25 equivalent amounts for 18 hours is followed by Steps 1-3 of the recouple program 2 and an additional coupling of 18 hours using the original (saved) coupling solution. This effects >99% complete reaction, preserving their supply. The isobutyryl N-terminal group is added by in situ formation of the symmetrical anhydride, using 5.0 equivalents of isobutyric acid and 2.5 equivalents of DCC. No HBT is used and the coupling is performed in CH$_2$Cl$_2$ alone for 30 minutes, followed by a similar recouple for 60 minutes. The DNP-protected group on His is removed in a final step by 10% thiophenol in DMF according to the program set out further below.

Step B:
IBU-His-Pro-Phe-Hcys(ACM)-Sta-Leu-Phe-OCH$_3$

The completed resin from Step A above, approximately 3.5 g, is suspended in 50 ml dry methanol (MeOH) under N$_2$, to which 5 ml diisopropylethylamine (DIPEA) is added. The suspension is stirred for 40 hours, filtered, and the resin washed with CH$_2$Cl$_2$ and MeOH. The combined filtrates are evaporated to give 3.3 g of a crude white residue. This proves to be predominantly a single compound by TLC, 80:20:2:1 chloroform:methanol:water:acetic acid.

Step C:
IBU-His-Pro-Phe-Hcys(ACM)-Sta-Leu-Phe-NH-CH$_2$-CH$_2$-S-ACM

The crude ester material from Step B is hydrolyzed in

N—Isobutyrl-L-Histidyl-L-Prolyl-L-Phenylalanyl-L-Homocysteinyl-(3S,4S)—Statyl-L-Leucyl-L-Phenyl-alanyl-2-Thioethylamide The title peptide, where the bracket beneath the name indicates the points of cyclization from L-Homocysteine (Hcys) to the thioethylamide by a disulfide link, was prepared by a combination of solid phase and solution methods.

Step A:
N-Isobutyryl-L-His-L-Pro-L-Phe-L-Hcys(ACM)-(3S,4S)-Sta-L-Leu-L-Phe-O-Resin The title peptide resin is prepared by standard solid phase methodology as described in Erickson and Merrifield, *Proteins*, 3rd ed., 2, 257-527 (1971), using a Beck- 50 ml 1:1, water/dioxane with 1 equivalent of 1N NaOH added slowly over 2 hours. The solution is then extracted once with CH$_2$Cl$_2$, after evaporation of the dioxane, and the pH adjusted in the water layer to the isoelectric point, about pH 5.5. The Zwitterion is then extracted with n-butanol and the n-butanol is evaporated to give IBU-His-Pro-Phe-Hcys(ACM)-Sta-Leu-Phe-OH. A portion of this free acid is dissolved in DMF and cooled to 0° C. To this solution is added 2.5 equivalents of diphenylphosphorylazide, 1.0 equivalents of 2-S-acetamidomethylethylamine, and 10 equivalents of NaHCO$_3$. The 2-S-acetamidomethylethylamine is obtained from 2-aminoethanethiol by S-acetamidomethylation accorded to the procedure described by P. Marbach and J. Rudinger, Helv. Chim. Acta. 57, 404 (1974) for cysteine. This suspension is stirred for two days at 5° C. and evaporated. The residue is washed in ethylacetate with water, dried, and evaporated to give the crude title compound which is precipitated from CHCl$_3$/EtOAc with hexanes and dried.

Step D: IBU—His—Pro—Phe—Hcys—Sta—Leu—Phe—NH—CH$_2$—CH$_2$—S—
                                    |_____|

Although the material from Step C contains several impurities, including reactants used in the coupling reactions, it is suitable for cyclization. An amino acid analysis of the crude material from Step C showed the amino acids in the correct ratios: His$_{1.01}$Pro$_{1.04}$Phe$_{1.95}$-Sta$_{0.97}$Leu$_{1.03}$ and Hcys—. A 0.77 g portion of crude material from Step C was dissolved in 520 ml of 80% acetic acid to which was added with stirring a 130 ml solution in 80% acetic acid of 1.65 g (about 10 equivalents) iodine. This orange solution was stirred for 10 minutes and quenched by addition of 5 g zinc dust. After 2 minutes, the solution was colorless and the solids were filtered off. The solution was evaporated at 40° C. to an oily residue. This residue was dissolved in 50 ml n-butanol and washed with 5% NaHCO$_3$ repeatedly. The n-butanol was concentrated and dissolved in 50% acetic acid and applied to a Sephadex G25 column and eluted with the same solvent. The peak eluting at the expected monomer position based upon molecular weight was collected and evaporated to give 0.300 g of material still impure by TLC and HPLC. TLC showed predominantly one material at R$_f$=0.38, 80:20:2:1, chloroform:methanol:water:acetic acid, with impurities streaking above and below. This crude material was purified by silica gel chromatography in 100:20:2:1, chloroform:methanol:water:acetic acid to give 95 mg of pure title compound after precipitation from CHCl$_3$/hexanes and drying. TLC: single spot. HPLC: 95.5% pure. Elemental analysis calculated for

| C$_{53}$H$_{76}$N$_{10}$O$_9$S$_2$.2H$_2$O: | | |
|---|---|---|
| | C | H | N |
| Calc. | 58.00 | 7.34 | 12.76 |
| Found | 57.96 | 7.47 | 12.44 |

Spinco: His$_{1.02}$ Pro$_{0.92}$ Phe$_{2.04}$ Sta Leu$_{1.01}$ and Hcys $^1$H NMR — 360 MHz consistent with structure.

SCHEDULE OF STEPS FOR 2 MMOL RUN

| Step | Solvent/Reagent | Vol. (ml) | Mix time (min) |
|---|---|---|---|
| Coupling Program 1 | | | |
| 1 | CH$_2$Cl$_2$ | 6 × 20 | 2 |
| 2 | 40% TFA in CH$_2$Cl$_2$ | 1 × 20 | 2 |
| 3 | 40% TFA in CH$_2$Cl$_2$ | 1 × 20 | 25 |
| 4 | CH$_2$Cl$_2$ | 3 × 20 | 2 |
| 5 | 10% TEA in CH$_2$Cl$_2$ | 2 × 20 | 5 |
| 6 | CH$_2$Cl$_2$ | 3 × 20 | 2 |
| 7 | BOC-amino acid, HBT | 20 | 5 |
| | in 1:1 DMF/CH$_2$Cl$_2$ | | |
| 8 | 1.0 M DCCI in CH$_2$Cl$_2$ | 5 | 30 |
| 9 | DMF | 1 × 20 | 2 |
| 10 | MeOH | 2 × 20 | 2 |
| 11 | CH$_2$Cl$_2$ | 1 × 20 | 2 |
| Re-Couple Program 2 | | | |
| 1 | CH$_2$Cl$_2$ | 1 × 20 | 2 |
| 2 | 10% TEA in CH$_2$Cl$_2$ | 2 × 20 | 5 |
| 3 | CH$_2$Cl$_2$ | 3 × 20 | 2 |
| 4 | BOC-amino acid, HBT | 20 | 5 |
| | in 1:1 DMF/CH$_2$Cl$_2$ | | |
| 5 | 1.0 M DCCI in CH$_2$Cl$_2$ | 15 | 60 |
| 6 | DMF | 1 × 20 | 2 |
| 7 | MeOH | 2 × 20 | 2 |
| 8 | CH$_2$Cl$_2$ | 5 × 20 | 2 |
| Program 3 (DNP removal) | | | |
| 1 | CH$_2$Cl$_2$ | 1 × 20 | 2 |
| 2 | DMF | 2 × 20 | 2 |
| 3 | 10% phenylthiol in DMF | 1 × 20 | 25 |
| 4 | DMF | 1 × 20 | 2 |
| 5 | 10% TEA in CH$_2$Cl$_2$ | 1 × 20 | 2 |
| 6 | DMF | 2 × 20 | 2 |
| 7 | 10% phenylthiol in DMF | 1 × 20 | 25 |
| 8 | DMF | 3 × 20 | 2 |
| 9 | MeOH | 2 × 20 | 2 |
| 10 | CH$_2$Cl$_2$ | 2 × 20 | 2 |
| 11 | MeOH | 2 × 20 | 2 |
| 12 | CH$_2$Cl$_2$ | 2 × 20 | 2 |
| 13 | MeOH | 2 × 20 | 2 |

EXAMPLE 3

N—Isobutyryl-L-Histidyl-L-Prolyl-L-Phenylalanyl-L-Cysteinyl-(3S,4S)—Statyl-L-Leucyl-L-Phenylalanyl-2-Thio-
|_____|
ethylamide Following the standard solid phase methodology described above in Example 2, the additional title inhibitory peptide of the present invention was prepared. Satisfactory amino acid analysis was obtained by Spinco method; and various other analytical methods were carried out which verified the structure of the peptide product.

EXAMPLE 4

Hog Renin Inhibition

An assay was carried out in order to determine the inhibitory potency of the peptides of the present invention. The assay measured the inhibition of hog kidney renin, and was in accordance with the procedure described in Rich et al., J. Med. Chem. 23:27, 1980, except that a pH of 7.3 was used. The results of the assay, illustrated in the table below, are expressed as I$_{50}$ values, which refers to the concentration of peptide inhibitor necessary to produce 50% inhibition of renin activity. This I$_{50}$ value is obtained typically by plotting data from four inhibitor concentrations. Pepstatin was used as an active control.

| Peptide | I$_{50}$ (M) |
|---|---|
| IBU—His—Pro—Phe—Cys—Sta—Leu—Phe—NH— <br>                                      \|___S——S___\| | 1.3 × 10$^{-7}$ |

| Peptide | I₅₀ (M) |
|---|---|
| IBU—His—Pro—Phe—Hcys—Sta—Leu—Phe—NH  with S—S bridge | $1.9 \times 10^{-7}$ |

What is claimed is:

1. A peptide of the formula:

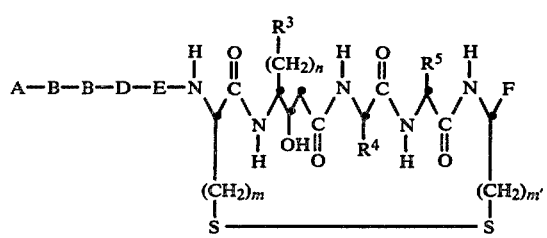
(I.)

wherein:

A is hydrogen; or

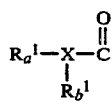

where
X is —O—;

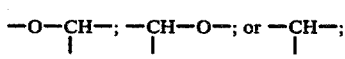

and $R_a^1$ and $R_b^1$ may be the same or different and are hydrogen; Y—(CH$_2$)$_p$— or Y—(CH$_2$)$_p$, —CH=CH—(CH$_2$)$_{p''}$, where Y is hydrogen; C$_{1-4}$alkyl; aryl; C$_{3-7}$cycloalkyl; or C$_{3-7}$cycloalkyl or aryl substituted with up to five members independently selected from the group consisting of C$_{1-8}$alkyl, trifluoromethyl, hydroxy, C$_{1-4}$alkoxy, and halo;

p is 0 to 5; and p' and p'' are independently 0 to 2; except that where X is —O—, only one of $R_a^1$ or $R_b^1$ is present;

B is absent; glycyl; sarcosyl; or

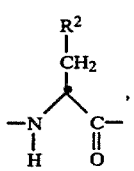

where R$^2$ is hydrogen; C$_{1-4}$ alkyl; hydroxy C$_{1-4}$ alkyl; aryl; aryl substituted with up to three members selected from the group consisting of C$_{1-4}$alkyl, trifluoromethyl, hydroxy, C$_{1-4}$alkoxy, and halo; indolyl; 4-imidazolyl; amino C$_{2-4}$ alkyl; guanidyl C$_{2-3}$ alkyl; or methylthiomethyl;

D is absent; or

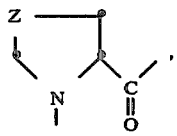

where Z is —(CH$_2$)$_q$— and q is 1 or 2; or —S—;
E is absent; or

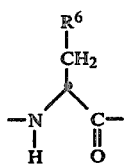

where R$^6$ is hydrogen; C$_{1-4}$alkyl; aryl; aryl C$_{1-4}$alkyl; or aryl C$_{1-4}$alkyl or aryl where the aryl portion is substituted with up to three members selected from the group consisting of C$_{1-4}$alkyl, trifluoromethyl, hydroxy, C$_{1-4}$alkoxy, and halo; or indolyl;

F is hydrogen;

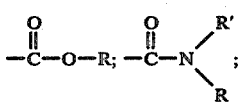

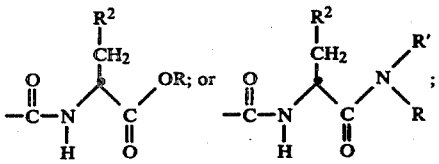

where R and R' are independently hydrogen or C$_{1-4}$alkyl;

R$^3$ is C$_{3-6}$ alkyl; C$_{3-7}$ cycloalkyl; aryl; or C$_{3-7}$cycloalkyl or aryl substituted with up to three members selected from the group consisting of C$_{1-4}$alkyl, trifluoromethyl, hydroxy, C$_{1-4}$alkoxy, and halo;

R$^4$ is hydrogen; or

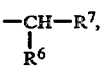

where R$^7$ is hydrogen; C$_{1-4}$alkyl; hydroxy; or C$_{3-7}$cycloalkyl; and R$^6$ is as defined above;

R$^5$ is hydrogen;

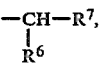

where $R^6$ and $R^7$ are as defined above; or —(CH$_2$-)$_r$—$R^8$, where r is 0 or 1–4; and $R^8$ is heterocyclic; heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino; guanidyl $C_{2-3}$alkyl; or amino $C_{1-4}$alkyl;

m and m' are independently 1 or 2;

n is 1 to 4; and wherein all of the asymmetric carbon atoms have an S configuration, except for those in the A, B, D, and F substituents, and at the junction of F, which may have an S or R configuration; and a pharmaceutically acceptable salt thereof.

2. A peptide according to claim 1 wherein the peptide is a member selected from the group consisting essentially of:

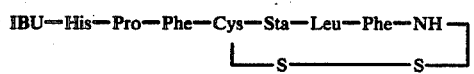

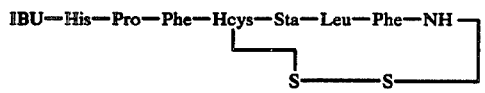

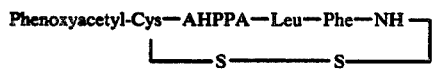

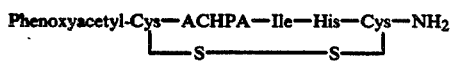

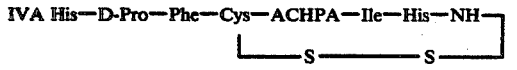

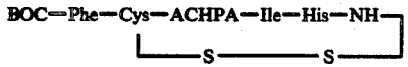

3. A pharmaceutical composition for treating renin-associated hypertension or hyperaldosteronism, comprising a pharmaceutical carrier and a therapeutically effective amount of a peptide of the formula:

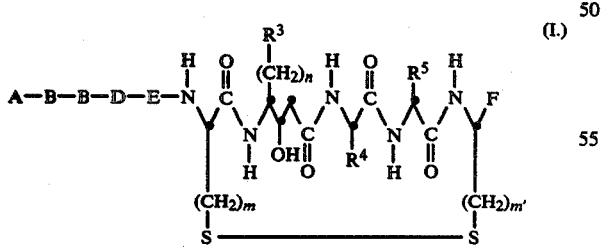

wherein:

A is hydrogen; or

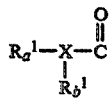

where

X is —O—;

$$-O-\overset{|}{CH}-; \quad -\overset{|}{CH}-O-; \quad \text{or} \quad -\overset{|}{CH}-;$$

and $R_a^1$ and $R_b^1$ may be the same or different and are hydrogen; Y—(CH$_2$)$_p$— or Y—(CH$_2$)$_{p'}$—CH=CH—(CH$_2$)$_{p''}$, where Y is hydrogen; $C_{1-4}$alkyl; aryl; $C_{3-7}$cycloalkyl; or $C_{3-7}$cycloalkyl or aryl substituted with up to five members independently selected from the group consisting of $C_{1-8}$alkyl, trifluoromethyl, hydroxy, $C_{1-4}$alkoxy, and halo;

p is 0 to 5; and p' and p'' are independently 0 to 2; except that where X is —O—, only one of $R_a^1$ or $R_b^1$ is present;

B is absent; glycyl; sarcosyl; or

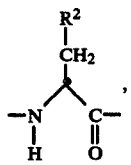

where $R^2$ is hydrogen; $C_{1-4}$ alkyl; hydroxy $C_{1-4}$ alkyl;

aryl; aryl substituted with up to three members selected from the group consisting of $C_{1-4}$alkyl, trifluoromethyl, hydroxy, $C_{1-4}$alkoxy, and halo; indolyl; 4-imidazolyl; amino $C_{2-4}$ alkyl; guanidyl $C_{2-3}$ alkyl; or methylthiomethyl;

D is absent; or

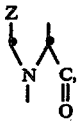

where Z is —(CH$_2$)$_q$— and q is 1 or 2; or —S—;

E is absent; or

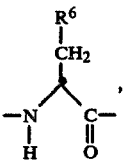

where $R^6$ is hydrogen; $C_{1-4}$alkyl; aryl; aryl $C_{1-4}$alkyl; or aryl $C_{1-4}$alkyl or aryl where the aryl portion is substituted with up to three members selected from the group consisting of $C_{1-4}$alkyl, trifluoromethyl, hydroxy, $C_{1-4}$alkoxy, and halo; or indolyl;

F is hydrogen;

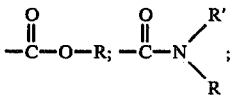

-continued

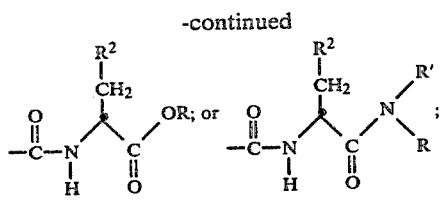

where R and R' are independently hydrogen or C$_{1-4}$alkyl;
R$^3$ is C$_{3-6}$ alkyl; C$_{3-7}$ cycloalkyl; aryl; or C$_{3-7}$cycloalkyl or aryl substituted with up to three members selected from the group consisting of C$_{1-4}$alkyl, trifluoromethyl, hydroxy, C$_{1-4}$alkoxy, and halo;
R$^4$ is hydrogen; or

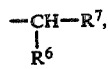

where R$^7$ is hydrogen; C$_{1-4}$alkyl; hydroxy; or C$_{3-7}$cycloalkyl; and R$^6$ is as defined above;
R$^5$ is hydrogen;

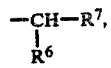

where R$^6$ and R$^7$ are as defined above; or —(CH$_2$)$_r$—R$^8$, where r is 0 or 1-4; and R$^8$ is heterocyclic; heterocyclic substituted with up to five members independently selected from the group consisting of C$_{1-6}$alkyl, hydroxy, trifluoromethyl; C$_{1-4}$alkoxy, halo, aryl, aryl C$_{1-4}$alkyl, amino, and mono- or di-C$_{1-4}$alkylamino; guanidyl C$_{2-3}$alkyl; or amino C$_{1-4}$alkyl;
m and m' are independently 1 or 2;
n is 1 to 4; and
wherein all of the asymmetric carbon atoms have an S configuration, except for those in the A, B, D, and F substituents, and at the junction of F, which may have an S or R configuration; and a pharmaceutically acceptable salt thereof.

4. A composition according to claim 3 wherein the peptide is a member selected from the group consisting essentially of:

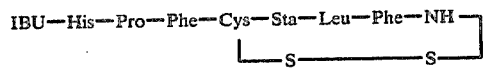

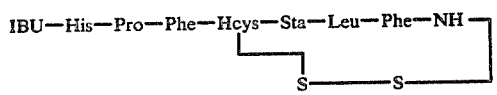

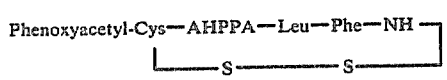

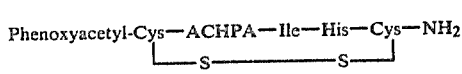

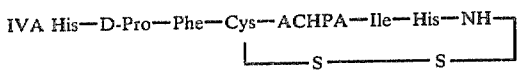

-continued

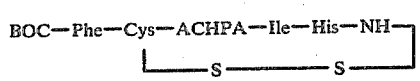

5. A method of treating renin-associated hypertension comprising administering to a patient in need of such treatment, a therapeutically effective amount of a peptide of the formula:

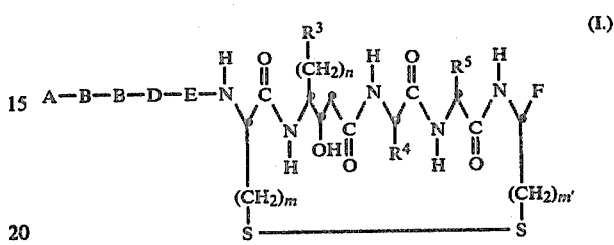

wherein:
A is hydrogen; or

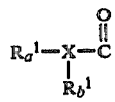

where
X is —O—; —O—CH—; —CH—O—; or —CH—; and R$_a^1$ and R$_b^1$ may be the same or different and are hydrogen; Y—(CH$_2$)$_p$— or Y—(CH$_2$)$_{p'}$—CH=CH—(CH$_2$)$_{p''}$, where Y is hydrogen; C$_{1-4}$alkyl; aryl; C$_{3-7}$cycloalkyl; or C$_{3-7}$cycloalkyl or aryl substituted with up to five members independently selected from the group consisting of C$_{1-8}$alkyl, trifluoromethyl, hydroxy, C$_{1-4}$alkoxy, and halo;
p is 0 to 5; and p' and p'' are independently 0 to 2; except that where X is —O—, only one of R$_a^1$ or R$_b^1$ is present;
B is absent; glycyl; sarcosyl; or

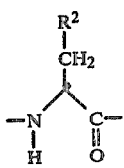

where R$^2$ is hydrogen; C$_{1-4}$ alkyl; hydroxy C$_{1-4}$ alkyl;
aryl; aryl substituted with up to three members selected from the group consisting of C$_{1-4}$alkyl, trifluoromethyl, hydroxy, C$_{1-4}$alkoxy, and halo; indolyl; 4-imidazolyl; amino C$_{2-4}$ alkyl; guanidyl C$_{2-3}$ alkyl; or methylthiomethyl;
D is absent; or

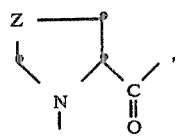

where Z is —(CH$_2$)$_q$— and q is 1 or 2; or —S—;
E is absent; or

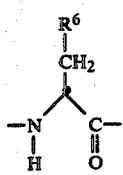

where R$^6$ is hydrogen; C$_{1-4}$alkyl; aryl; aryl C$_{1-4}$alkyl; or aryl C$_{1-4}$alkyl or aryl where the aryl portion is substituted with up to three members selected from the group consisting of C$_{1-4}$alkyl, trifluoromethyl, hydroxy, C$_{1-4}$alkoxy, and halo; or indolyl;
F is hydrogen;

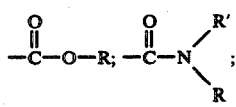

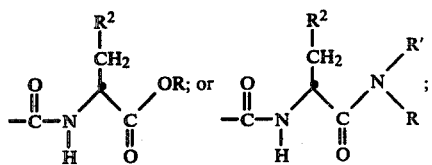

where R and R' are independently hydrogen or C$_{1-4}$alkyl;
R$^3$ is C$_{3-6}$ alkyl; C$_{3-7}$ cycloalkyl; aryl; or C$_{3-7}$cycloalkyl or aryl substituted with up to three members selected from the group consisting of C$_{1-4}$alkyl, trifluoromethyl, hydroxy, C$_{1-4}$alkoxy, and halo;
R$^4$ is hydrogen; or

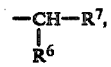

where R$^7$ is hydrogen; C$_{1-4}$alkyl; hydroxy; or C$_{3-7}$cycloalkyl; and R$^6$ is as defined above;
R$^5$ is hydrogen;

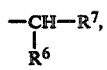

where R$^6$ and R$^7$ are as defined above; or —(CH$_2$)$_r$—R$^8$, where r is 0 or 1–4; and R$^8$ is heterocyclic; heterocyclic substituted with up to five members independently selected from the group consisting of C$_{1-6}$alkyl, hydroxy, trifluoromethyl, C$_{1-4}$alkoxy, halo, aryl, aryl C$_{1-4}$alkyl, amino, and mono- or di-C$_{1-4}$alkylamino; guanidyl C$_{2-3}$alkyl; or amino C$_{1-4}$alkyl;
m and m' are independently 1 or 2;
n is 1 to 4; and
wherein all of the asymmetric carbon atoms have an S configuration, except for those in the A, B, D, and F substituents, and at the junction of F, which may have an S or R configuration; and a pharmaceutically acceptable salt thereof.

6. A method according to claim 5 wherein the peptide is a member selected from the group consisting essentially of:

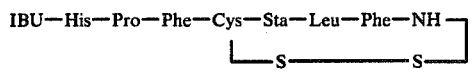

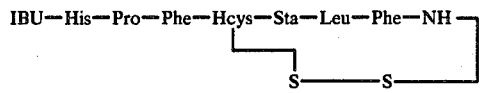

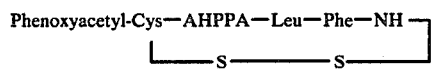

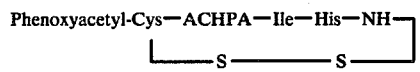

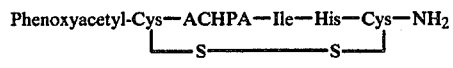

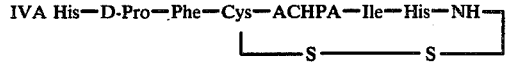

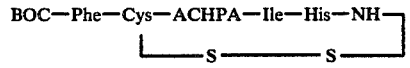

7. A method of treating renin-associated hyperaldosteronism, comprising administering to a patient in need of such treatment, a therapeutically effective amount of a peptide of the formula:

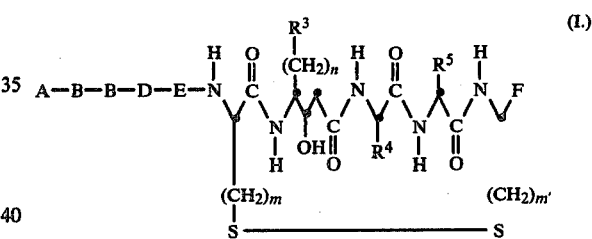

(I.)

wherein:
A is hydrogen; or

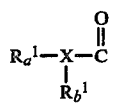

where
X is —O—;

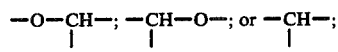

and R$_a$$^1$ and R$_b$$^1$ may be the same or different and are hydrogen; Y—(CH$_2$)$_p$— or Y—(CH$_2$)$_{p'}$—CH=CH—(CH$_2$)$_{p''}$, where Y is hydrogen; C$_{1-4}$alkyl; aryl; C$_{3-7}$cycloalkyl; or C$_{3-7}$cycloalkyl or aryl substituted with up to five members independently selected from the group consisting of C$_{1-8}$alkyl, trifluoromethyl, hydroxy, C$_{1-4}$alkoxy, and halo;
p is 0 to 5; and p' and p'' are independently 0 to 2; except that where X is —O—, only one of R$_a$$^1$ or R$_b$$^1$ is present;

B is absent; glycyl; sarcosyl; or

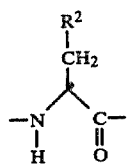

where $R^2$ is hydrogen; $C_{1-4}$ alkyl; hydroxy $C_{1-4}$ alkyl; aryl; aryl substituted with up to three members selected from the group consisting of $C_{1-4}$alkyl, trifluoromethyl, hydroxy, $C_{1-4}$alkoxy, and halo; indolyl; 4-imidazolyl; amino $C_{2-4}$ alkyl; guanidyl $C_{2-3}$ alkyl; or methylthiomethyl;

D is absent; or

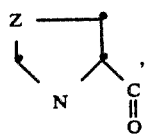

where Z is $-(CH_2)_q-$ and q is 1 or 2; or $-S-$;

E is absent; or

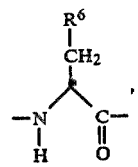

where $R^6$ is hydrogen; $C_{1-4}$alkyl; aryl; aryl $C_{1-4}$alkyl; or aryl $C_{1-4}$alkyl or aryl where the aryl portion is substituted with up to three members selected from the group consisting of $C_{1-4}$alkyl, trifluoromethyl, hydroxy, $C_{1-4}$alkoxy, and halo; or indolyl;

F is hydrogen;

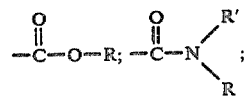

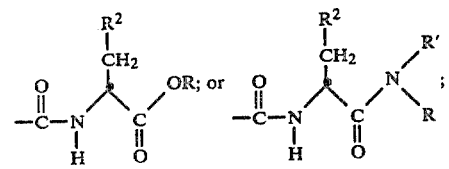

where R and R' are independently hydrogen or $C_{1-4}$alkyl;

$R^3$ is $C_{3-6}$alkyl; $C_{3-7}$ cycloalkyl; aryl; or $C_{3-7}$cycloalkyl or aryl substituted with up to three members selected from the group consisting of $C_{1-4}$alkyl, trifluoromethyl, hydroxy, $C_{1-4}$alkoxy, and halo;

$R^4$ is hydrogen; or

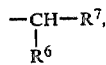

where $R^7$ is hydrogen; $C_{1-4}$alkyl; hydroxy; or $C_{3-7}$cycloalkyl; and $R^6$ is as defined above;

$R^5$ is hydrogen;

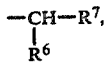

where $R^6$ and $R^7$ are as defined above; or $-(CH_2)_r-R^8$, where r is 0 or 1–4; and $R^8$ is heterocyclic; heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino; guanidyl $C_{2-3}$alkyl; or amino $C_{1-4}$alkyl;

m and m' are independently 1 or 2;

n is 1 to 4; and wherein all of the asymmetric carbon atoms have an S configuration, except for those in the A, B, D, and F substituents, and at the junction of F, which may have an S or R configuration; and a pharmaceutically acceptable salt thereof.

8. A method of determining the presence of renin-associated hypertension in a patient, comprising administering to such a patient, at a hypotensive dosage level and as a single dose, a peptide of the formula:

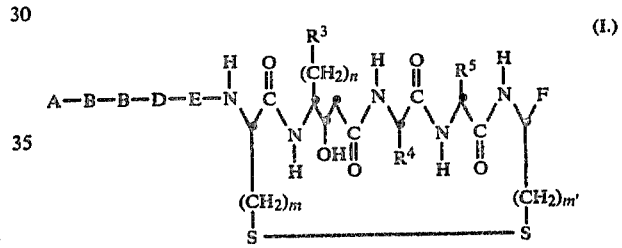 (I.)

wherein:

A is hydrogen; or

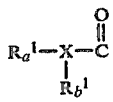

where

X is $-O-$;

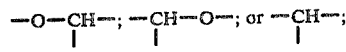

and $R_a^1$ and $R_b^1$ may be the same or different and are hydrogen; $Y-(CH_2)_p-$ or $Y-(CH_2)_{p'}-CH=CH-(CH_2)_{p''}$, where Y is hydrogen; $C_{1-4}$alkyl; aryl; $C_{3-7}$cycloalkyl; or $C_{3-7}$cycloalkyl or aryl substituted with up to five members independently selected from the group consisting of $C_{1-8}$alkyl, trifluoromethyl, hydroxy, $C_{1-4}$alkoxy, and halo;

p is 0 to 5; and p' and p" are independently 0 to 2; except that where X is $-O-$, only one of $R_a^1$ or $R_b^1$ is present;

B is absent; glycyl; sarcosyl; or

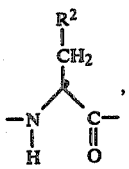

where $R^2$ is hydrogen; $C_{1-4}$ alkyl; hydroxy $C_{1-4}$ alkyl; aryl; aryl substituted with up to three members selected from the group consisting of $C_{1-4}$alkyl, trifluoromethyl, hydroxy, $C_{1-4}$alkoxy, and halo; indolyl; 4-imidazolyl; amino $C_{2-4}$ alkyl; guanidyl $C_{2-3}$ alkyl; or methylthiomethyl;

D is absent; or

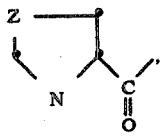

where Z is $-(CH_2)_q-$ and q is 1 or 2; or $-S-$;

E is absent; or

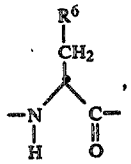

where $R^6$ is hydrogen; $C_{1-4}$alkyl; aryl; aryl $C_{1-4}$alkyl; or aryl $C_{1-4}$alkyl or aryl where the aryl portion is substituted with up to three members selected from the group consisting of $C_{1-4}$alkyl, trifluoromethyl, hydroxy, $C_{1-4}$alkoxy, and halo; or indolyl;

F is hydrogen;

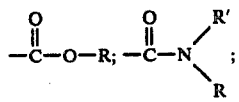

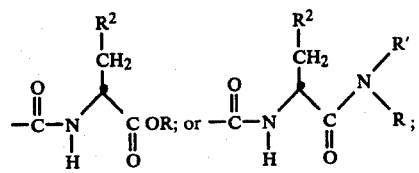

where R and R' are independently hydrogen or $C_{1-4}$alkyl;

$R^3$ is $C_{3-6}$ alkyl; $C_{3-7}$ cycloalkyl; aryl; or $C_{3-7}$cycloalkyl or aryl substituted with up to three members selected from the group consisting of $C_{1-4}$alkyl, trifluoromethyl, hydroxy, $C_{1-4}$alkoxy, and halo;

$R^4$ is hydrogen; or

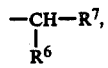

where $R^7$ is hydrogen; $C_{1-4}$alkyl; hydroxy; or $C_{3-7}$cycloalkyl; and $R^6$ is as defined above;

$R^5$ is hydrogen;

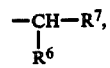

where $R^6$ and $R^7$ are as defined above; or $-(CH_2)_r-R^8$, where r is 0 or 1–4; and $R^8$ is heterocyclic; heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino; guanidyl $C_{2-3}$alkyl; or amino $C_{1-4}$alkyl;

m and m' are independently 1 or 2;

n is 1 to 4; and wherein all of the asymmetric carbon atoms have an S configuration, except for those in the A, B, D, and F substituents, and at the junction of F, which may have an S or R configuration; and a pharmaceutically acceptable salt thereof; followed by monitoring of said patient's blood pressure.

* * * * *